(12) United States Patent
Zaeper et al.

(10) Patent No.: US 8,600,679 B2
(45) Date of Patent: Dec. 3, 2013

(54) SYSTEM AND METHOD TO LOCATE, MONITOR AND QUANTIFY FRICTION BETWEEN A DRILLSTRING AND A WELLBORE

(75) Inventors: Ralf Zaeper, Hannover (DE); Roland May, Celle (DE); John D Macpherson, Spring, TX (US); Thomas Dahl, Schwuelper (DE)

(73) Assignee: Baker Hughes Incorporated, Houston, TX (US)

( * ) Notice: Subject to any disclaimer, the term of this patent is extended or adjusted under 35 U.S.C. 154(b) by 397 days.

(21) Appl. No.: 12/389,441

(22) Filed: Feb. 20, 2009

(65) Prior Publication Data

US 2009/0216453 A1    Aug. 27, 2009

Related U.S. Application Data

(60) Provisional application No. 61/031,755, filed on Feb. 27, 2008.

(51) Int. Cl.
*G01V 3/38*    (2006.01)
(52) U.S. Cl.
USPC ............. 702/6; 702/9; 702/11; 702/16; 73/9; 73/152.46; 73/152.48; 73/152.49; 73/152.59; 175/40; 340/854.1

(58) Field of Classification Search
USPC ........ 702/6, 9, 11, 16; 175/45, 40; 340/854.1; 73/9, 152.46, 152.48, 152.49, 152.59
See application file for complete search history.

(56) References Cited

U.S. PATENT DOCUMENTS

| | | | |
|---|---|---|---|
| 6,176,323 B1 * | 1/2001 | Weirich et al. | 175/40 |
| 2004/0149471 A1 | 8/2004 | Hall et al. | |
| 2005/0194185 A1 * | 9/2005 | Gleitman | 175/45 |
| 2005/0200498 A1 * | 9/2005 | Gleitman | 340/854.4 |
| 2006/0260801 A1 | 11/2006 | Hall et al. | |
| 2007/0126596 A1 | 6/2007 | Hall et al. | |

OTHER PUBLICATIONS

Santos, et al. "Consequences and Relevance of Drillstring Vibration on Wellbore Stability". SPE/IADC 52820. SPE/IADC Drilling Conference held in Amsterdam, Holland, Mar. 9-11, 1999.

* cited by examiner

*Primary Examiner* — Alexander H Taningco
*Assistant Examiner* — Paul D Lee
(74) *Attorney, Agent, or Firm* — Cantor Colburn LLP

(57) ABSTRACT

Disclosed herein is a method of locating and quantifying friction between a drillstring and a wellbore. The method includes, positioning a plurality of sensors within a wellbore, communicatively coupling the plurality of sensors, monitoring signals from the plurality of sensors, logging the sensed signals versus time versus depth of each of the plurality of sensors, locating at least one friction zone along the drillstring within the wellbore based on the logging and quantifying friction in the at least one friction zone based on the logging.

20 Claims, 3 Drawing Sheets

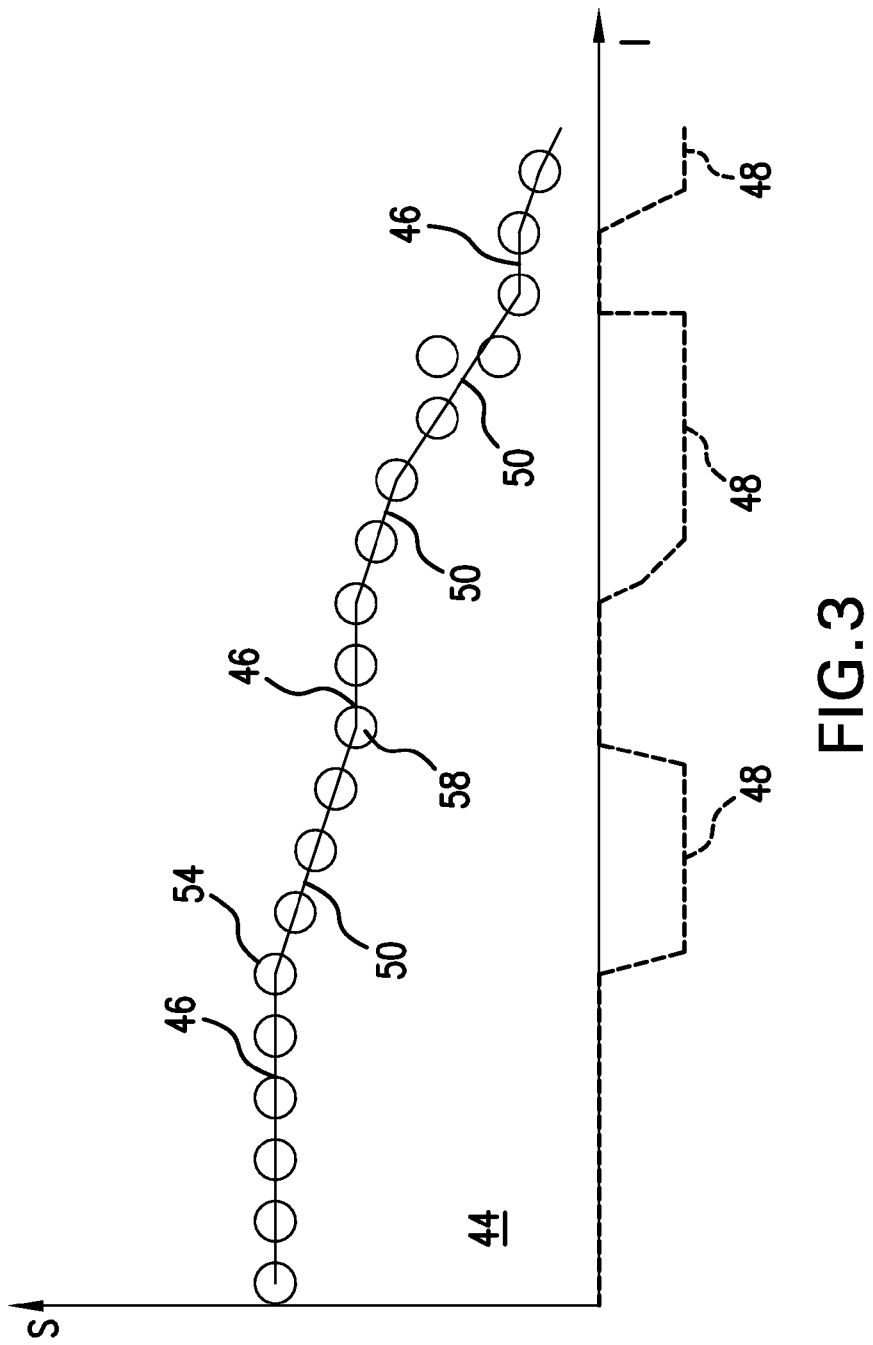

SYSTEM AND METHOD TO LOCATE, MONITOR AND QUANTIFY FRICTION BETWEEN A DRILLSTRING AND A WELLBORE

CROSS REFERENCE TO RELATED APPLICATIONS

Under 35 U.S.C. §119(e), this application claims the benefit of U.S. Provisional Application No. 61/031,755, filed Feb. 27, 2008, the entire disclosure of which is incorporated herein by reference.

BACKGROUND OF THE INVENTION

Successfully recovering the maximum amount of hydrocarbon production from a well is largely dependent upon characteristics of the wellbore drilled into the earth formation. How accurately a well operator understands the conditions that affect the drilling operation can have a significant effect on efficiency and on the ultimate production from a well. As such, tools to increase knowledge of the effects of the wellbore on the drillstring during drilling are of interest to well operators.

BRIEF DESCRIPTION OF THE INVENTION

Disclosed herein is a method of locating and quantifying friction between a drillstring and a wellbore. The method includes: positioning a plurality of sensors within a wellbore, communicatively coupling the plurality of sensors, monitoring signals from the plurality of sensors, logging the sensed signals versus time versus depth of each of the plurality of sensors, locating at least one friction zone along the drillstring within the wellbore based on the logging and quantifying friction in the at least one friction zone based on the logging.

Further disclosed herein is a downhole drillstring friction quantification and location system. The system includes: a plurality of sensors positioned along the drillstring, and a processor in communication with the plurality of sensors. The processor is configured to track a depth of each of the plurality of sensors based on estimated drillstring weight and downhole temperatures. The processor is further configured to adjust the tracked depth based on actual sensed data from the plurality of sensors and determine a location of at least one friction zone based upon deviations of parameters sensed by the plurality of sensors from estimated values for those parameters.

BRIEF DESCRIPTION OF THE DRAWINGS

The following descriptions should not be considered limiting in any way. With reference to the accompanying drawings, like elements are numbered alike:

FIG. 3 depicts a graph of a sensed parameter versus depth for a drillstring within a wellbore.

DETAILED DESCRIPTION OF THE INVENTION

A detailed description of one or more embodiments of the disclosed apparatus and method are presented herein by way of exemplification and not limitation with reference to the Figures.

Figure 1:
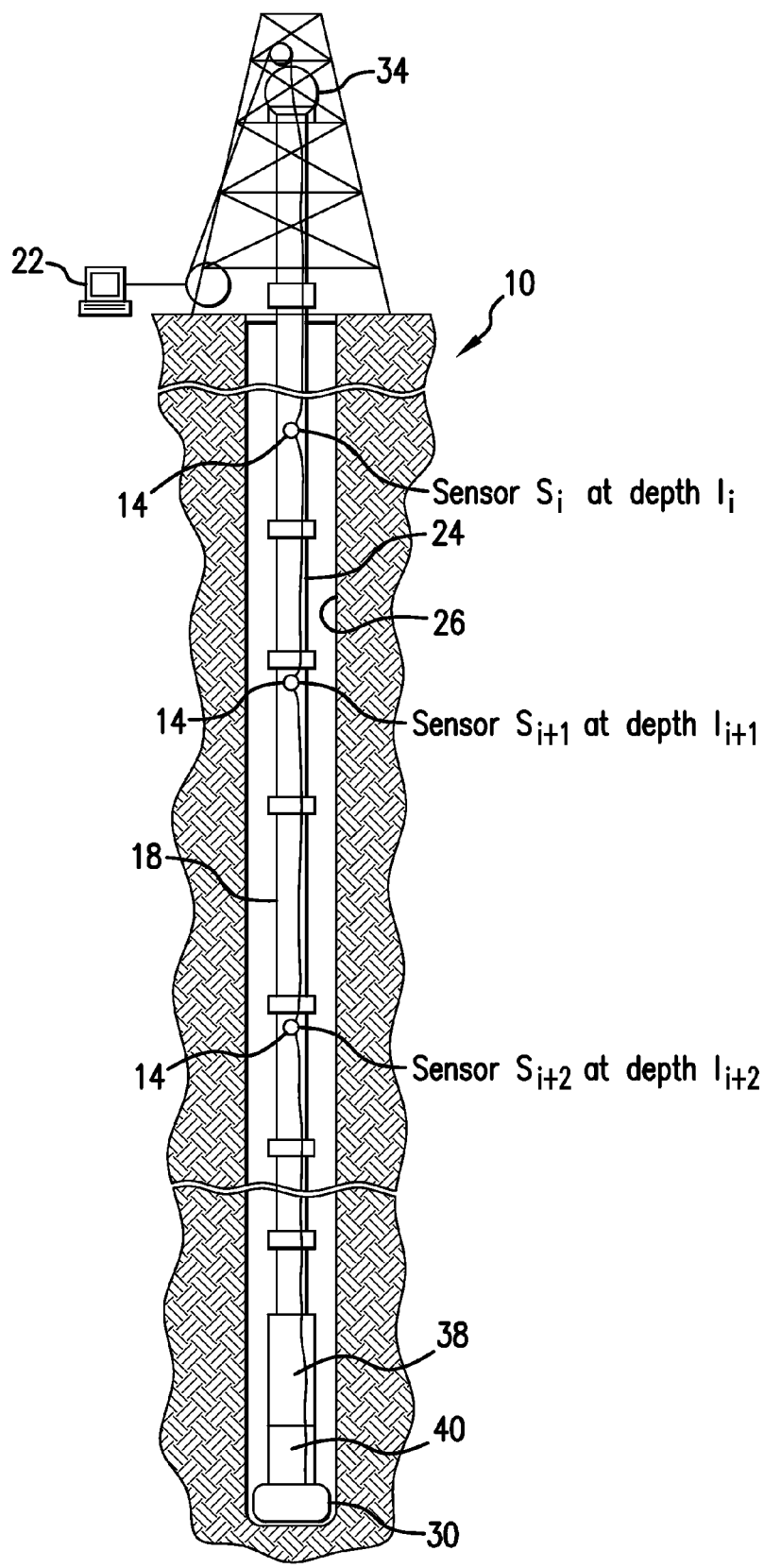
FIG. 1 depicts a schematical representation of a drillstring friction location and quantification system disclosed herein.

Referring to FIG. 1, an embodiment of a downhole drillstring friction quantification, monitoring and/or location system 10 is illustrated. The system 10 includes a plurality of sensors 14 positioned along a drillstring 18 and a processor 22 in communication with the sensors 14. In one embodiment, the processor 22 is in high data rate communication with the sensors 14, for example through a high bandwidth channel such as via a wired pipe 24. The drillstring 18 is shown located within wellbore 26. The sensors 14, distributed along the drillstring 18 may be configured to monitor several characteristics including torque, weight, temperature, pressure and magnetic fields, for example. The sensors 14 can be identified by their relative location from surface such as $S_i$ at a depth of $l_i$, for example. As such, the sensors 14 in descending order from surface would be $S_{i+1}$, $S_{i+2}$, $S_{i+3}$ ... at depths $l_{i+1}$, $l_{i+2}$, $l_{i+3}$ ... respectively.

In one embodiment, the positions of the sensors 14 along the drillstring 18 are monitored with some depth uncertainty due mainly to unexpected axial stress, floating effects and temperature variation but may be considered as initially known sufficiently accurate. During drilling operations the drillstring 18 is moved along the wellbore axis over time during, for example, drilling, tripping and reaming. The drilling process is influenced by applying torque M and weight W on a drill bit 30 (WOB) or weight on a reamer 30 (WOR) or other downhole components. Torque is generally applied, for example, by means of a surface rotation device 34 ($M_S$) and optionally a downhole rotation device such as a motor or turbine 38 ($M_{DH}$). WOB and WOR are adjusted by balancing drillstring 18 weight and hook load (HL) all resulting in a certain weight and torque distribution in the drillstring 18. The surface inputs, $M_S$, HL and fluid flow rate (FR), can be easily measured or calculated. In one embodiment, calculating $M_{DH}$ includes deriving values from device data sheets for known flow rates. WOB and torque-on-bit (TOB) can be measured by dynamic sensors located, for example, in the bottom hole assembly 40 (BHA). Drillstring 18 weight and torque as well as other conditions along the drillstring 18 and wellbore 26, however, are typically only available through static and dynamic models for an idealized system with well known geometries and earth formation properties. These idealized properties only partly match reality.

Figure 2:
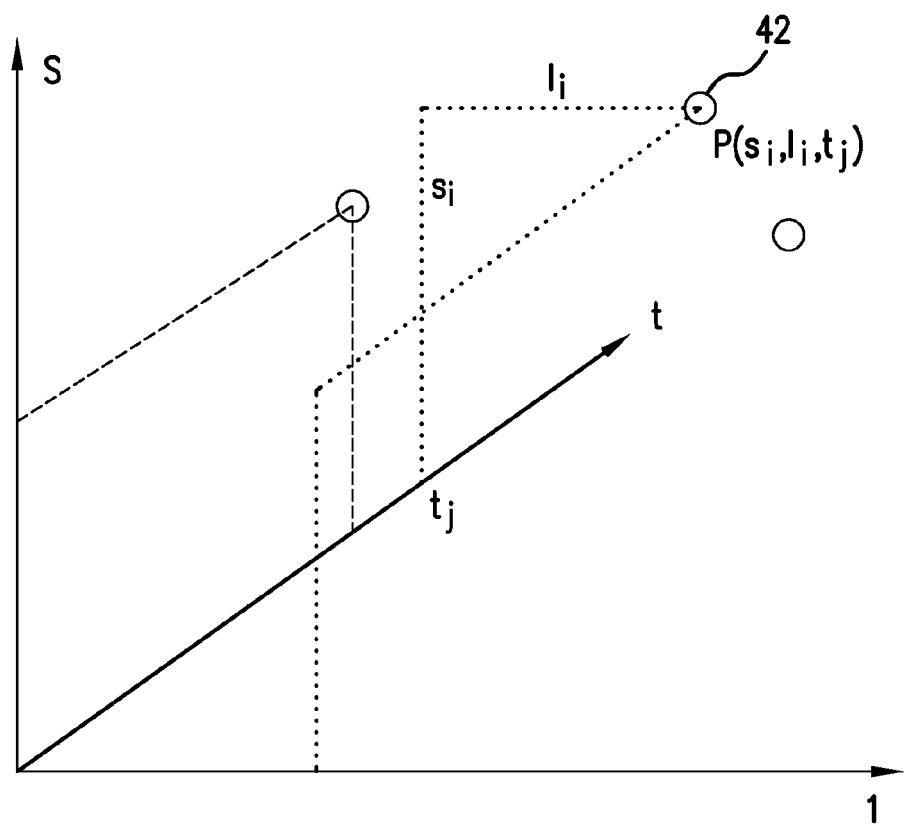
FIG. 2 depicts a multidimensional graph of sensed parameter versus depth of sensor versus time.

Referring to FIG. 2, to derive a more realistic picture of the drilling environment, the sensors 14 may be sampled at various times $t_j$ (j=0 ... m, with m elements of the natural numbers N) and sensor depth $l_i$ recorded for the same times $t_j$. With these readings and records, a multidimensional log space can be completed with points $P(S_{ki}, l_i, t_j)$ over time and drillstring 18 movement (where k indicates the sensor type), where one dimension is time $t_j$, one is sensor depth $l_i$ (measurement depth), and other dimensions are the outputs of the various sensors 14. Uncertainties of readings of the sensors 14, depth and time are denoted by an ellipsoid of uncertainty 42. Coordinates of the various points can and should be corrected for possible dynamic effects and input variations, such as, changes in surface torque via torque sensor 14 readings, for example.

Referring to FIG. 3, a typical depth based log can be achieved by simply projecting the points of one type of sensor 14 onto a sensor-depth plane 44. Measurements for a specific depth may be averaged, or filtered otherwise. Using multiple sensors 14 along the drillstring 18 allows one to draw complete depth logs without moving the string over the entire measured well depth. The records may also be used to show a time dependency of the log progression, for example. Examples of depth logs include torque logs over measured depth when using torque sensors 14, stress logs over measured depth when using strain gage arrays or magnetic field sensor arrays and weight logs over measured depth when using axial strain gages or magnetic sensor arrangements measuring axial stress. Temperature sensors could be used to display temperature distribution along the well path, and pressure sensors could be used in order to derive measured pressure-depth correlation logs.

Results may be used to reconsider initial assumptions, for example, depths may be calculated based on the mechanical loads and temperatures fed back into the initial string and well model from the measurements in order to minimize uncertainties.

Projected measurement points may be newly ascending, enumerated along a depth axis, starting from surface and denoted by exemplary identifiers $(S(l_0), S(l_1) \ldots S(l_q)=S_0, S_1 \ldots S_q$ (with q elements of the natural number N). In the case of torque and weight (simply derived, for examples) from axial stress readings and drillstring geometry) the log would be expected to show a steady and (depending on wellbore 26 and drillstring 18 geometry) partly linear approximated progression respectively with a constant gradient (or slope) 46 in the absence of friction:

$$\frac{S(l_{i+1}) - S(l_i)}{l_{i+1} - l_i} \approx const. \qquad 1$$

This means friction zones 48, or spots of noticeably greater friction, can be detected with a gradient log derived from weight and torque logs. The friction zones 48 can be assumed to reside where an alternate gradient 50 exists that deviates from the expected constant gradient 46. A magnitude of the frictional zones 48 can be determined by the difference between the gradient 50 and the gradient 46. Additionally, the depths where the gradient 46 transitions to the gradient 50 can indicate a beginning 54 of the friction zone 48. Similarly, where the gradient 50 transitions to the gradient 46 can indicate an ending 58 of the friction zone 48. Comparison with mechanical models identifying wall contact or other static and dynamic drillstring 18 to wellbore 26 interactions causing high friction, may allow mapping wellbore 26 intervals that have a weight or torque transfer problem due to swelling and deviated wellbore 26 profiles, such as local doglegs and cutting accumulation, for example.

Other applications utilizing the sensors 14 spaced apart along the drillstring 18 include determination of differential sticking, identification of where a pipe is stuck and weight and torque transfer across an active drilling element, such as a reamer, for example.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What is claimed is:

1. A method of locating and quantifying friction between a drillstring and a wellbore, comprising:

generating a model of at least one of drillstring weight and torque for at least one predetermined depth for an idealized system with known geometries and earth formation properties;
positioning a plurality of sensors within a wellbore;
communicatively coupling the plurality of sensors;
monitoring signals from the plurality of sensors;
logging the sensed signals versus time versus depth of each of the plurality of sensors to generate a measured parameter log to generate a multi-dimensional log space;
adjusting the model based on the multi-dimensional log space by calculating apparent depths based on at least one of sensed mechanical loads and temperatures fed back into the model, the at least one of the sensed mechanical loads and temperatures sensed by the plutality of sensors within the wellbore; and
locating at least one friction zone along the drillstring within the wellbore based on detecting changes in the adjustments to the model over time.

2. The method of claim 1, wherein a depth of the at least one friction zone is correlated with a location of a transition in a measured parameter log.

3. The method of claim 1, wherein friction in the at least one friction zone is quantified by a deviation of a gradient from an estimated gradient of the sensor signals versus depths logs.

4. The method of claim 1, wherein a depth of the at least one friction zone is determined by the depths of sensors providing signals that deviate from values anticipated by estimates.

5. The method of claim 1, wherein the friction in the at least one friction zone is quantified by an amount of deviation of sensed values as compared to values anticipated by estimates.

6. The method of claim 1, further comprising tracking a depth of each of the plurality of sensors during well operations.

7. The method of claim 6, further comprising adjusting tracked sensor depths based on load measurements from the plurality of sensors.

8. The method of claim 6, further comprising adjusting tracked sensor depths based on temperature measurements from the plurality of sensors.

9. The method of claim 1, wherein the communicatively coupling the plurality of sensors is via wired pipe.

10. The method of claim 1, wherein the communicatively coupling the plurality of sensors is via a high bandwidth channel as part of the drill string arrangement.

11. The method of claim 1, wherein the plurality of sensors sense torque.

12. The method of claim 1, wherein the plurality of sensors sense strain.

13. The method of claim 1, wherein the plurality of sensors sense at least one of temperature and pressure.

14. The method of claim 1, further comprising distributing the plurality of sensors along the drillstring.

15. The method of claim 1, further comprising communicatively coupling a processor to the plurality of sensors.

16. The method of claim 1, further comprising monitoring timely changes of sensor measurements.

17. A downhole drillstring friction quantification and location system, comprising:
a plurality of sensors positioned along the drillstring; and
a processor in communication with the plurality of sensors, the processor configured to generate a model of at least one of drillstring weight and torque for at least one predetermined depth for an idealized system with known geometries and earth formation properties, receive parameter data from each of the plurality of sensors, to log the parameter data versus time versus depth to generate a measured parameter log, to generate a multi-dimensional log space based on the measured parameter log, to adjust the model based on the multi-dimensional log space by calculating apparent depths based on at least one of sensed mechanical loads and temperatures fed back into the model, the at least one of the sensed mechanical loads and temperatures sensed by the plurality of sensors positioned along the drillstring, and the processor further configured to determine a location of at least one friction zone based on detecting changes in the adjustments to the model over time.

18. The system of claim 17, wherein the processor is further configured to determine a weight and torque distribution along the drill string.

19. The system of claim 17, wherein the processor is further configured to quantify friction of the at least one friction zone based upon deviations of parameters sensed by the plurality of sensors from estimated values for those parameters.

20. The system of claim 17, wherein the communication is a high data rate communication between the plurality of sensors and the processor via wired pipe.

\* \* \* \* \*